(12) United States Patent
Uzbelger Feldman (10) Patent No.: US 8,430,563 B2
(45) Date of Patent: Apr. 30, 2013

(54) DENTAL FLUOROSCOPIC IMAGING SYSTEM

(75) Inventor: Daniel Uzbelger Feldman, Downingtown, PA (US)

(73) Assignee: Real Time Imaging Technologies, LLC, Charlotte, NC (US)

( * ) Notice: Subject to any disclaimer, the term of this patent is extended or adjusted under 35 U.S.C. 154(b) by 0 days.

(21) Appl. No.: 12/653,964

(22) Filed: Dec. 22, 2009

(65) Prior Publication Data

US 2011/0150185 A1 Jun. 23, 2011

(51) Int. Cl.
*A61B 6/14* (2006.01)
*G21K 3/00* (2006.01)

(52) U.S. Cl.
USPC ............................................. 378/191; 378/38

(58) Field of Classification Search .............. 378/38–40, 378/62, 91, 98, 98.8, 189–191; 250/370.01, 250/370.08, 370.09, 370.11, 370.12, 370.14
See application file for complete search history.

(56) References Cited

U.S. PATENT DOCUMENTS

| | | | |
|---|---|---|---|
| 4,593,400 A | 6/1986 | Mouyen | |
| 4,965,455 A | 10/1990 | Schneider et al. | |
| 5,049,987 A | 9/1991 | Hoppenstein | |
| 5,262,649 A | 11/1993 | Antonuk et al. | |
| 5,382,798 A | 1/1995 | Mouyen | |
| 5,434,418 A | 7/1995 | Schick | |
| 5,510,623 A | 4/1996 | Sayag et al. | |
| 5,519,751 A | 5/1996 | Yamamoto et al. | |
| 5,610,404 A | 3/1997 | Possin | |
| 5,648,654 A | 7/1997 | Possin | |
| 5,693,948 A | 12/1997 | Sayed et al. | |
| 5,773,832 A | 6/1998 | Sayed et al. | |
| 5,834,782 A | 11/1998 | Schick et al. | |

(Continued)

FOREIGN PATENT DOCUMENTS

| | | |
|---|---|---|
| WO | WO/2004/110277 | 12/2004 |
| WO | WO/2005/072615 | 8/2005 |
| WO | WO/2005/110234 | 11/2005 |
| WO | WO 2007046372 A1 * | 4/2007 |

OTHER PUBLICATIONS

Eisenberg RL. Radiology. An illustrated history. 1895 Centennial 1995: Mosby Year Book 1992;4:51-78.

(Continued)

*Primary Examiner* — Anastasia Midkiff
(74) *Attorney, Agent, or Firm* — Tillman Wright, PLLC; Chad D. Tillman; Jeremy C. Doerre (57) ABSTRACT

The dental fluoroscopic imaging system includes a flat panel detector comprised by a gamma-rays or x-rays converter, a plate, a collector, a processing unit and a transmitter suitable for 2D intraoral/extraoral and 3D extraoral dental fluoroscopy. The x-ray converter contains a material capable of transforming the low dose gamma rays or x-rays beam received from an emitter after going through the dental examination area into electrical signals or a light image consequent with the radiographed image. The plate transmits the electric signals or light image to a collector which amplifies it and sends it to a processing unit and then to transmitter designed to transfer digital images sequentially to a host computer and software which can acquire, process, transform, record, freeze and enhance 2D and 3D images of video frame rates. Two dimensional images are obtained while using a C-arm/U-arm configuration while 3D images are obtained while using the O-arm configuration.

23 Claims, 5 Drawing Sheets

U.S. PATENT DOCUMENTS

| | | | |
|---|---|---|---|
| 5,841,830 | A | 11/1998 | Barni et al. |
| 5,864,146 | A * | 1/1999 | Karellas ............... 250/581 |
| 5,912,942 | A | 6/1999 | Schick et al. |
| 5,949,848 | A | 9/1999 | Gilblom |
| 5,962,856 | A | 10/1999 | Zhao et al. |
| 6,404,854 | B1 | 6/2002 | Carroll et al. |
| 6,543,936 | B2 | 4/2003 | Feldman |
| 6,566,809 | B1 | 5/2003 | Fuchs et al. |
| 6,717,174 | B2 | 4/2004 | Karellas |
| 7,016,461 | B2 | 3/2006 | Rotondo et al. |
| 7,039,156 | B2 * | 5/2006 | Arai et al. ............... 378/39 |
| 7,136,452 | B2 | 11/2006 | Spartiotis et al. |
| 7,197,109 | B2 | 3/2007 | Rotondo et al. |
| 7,211,817 | B2 | 5/2007 | Moody |
| 7,231,014 | B2 | 6/2007 | Levy |
| 7,274,766 | B2 * | 9/2007 | Kaipio et al. ............ 378/22 |
| 7,319,736 | B2 | 1/2008 | Rotondo et al. |
| 7,322,746 | B2 | 1/2008 | Beckhaus et al. |
| 7,323,692 | B2 | 1/2008 | Rowlands et al. |
| 7,336,763 | B2 | 2/2008 | Spartiotis et al. |
| 7,426,258 | B1 | 9/2008 | Zweig |
| 7,563,026 | B2 | 7/2009 | Mandelkern et al. |
| 7,596,205 | B2 | 9/2009 | Zhang et al. |
| 7,608,834 | B2 | 10/2009 | Boucly et al. |
| 7,615,754 | B2 | 11/2009 | Liu et al. |
| 7,629,587 | B2 | 12/2009 | Yagi et al. |
| 2006/0008050 | A1 * | 1/2006 | Massie ............... 378/38 |
| 2006/0151708 | A1 * | 7/2006 | Bani-Hashemi et al. 250/370.11 |
| 2006/0203959 | A1 * | 9/2006 | Spartiotis et al. ......... 378/38 |
| 2008/0019476 | A1 * | 1/2008 | Mirzayan ............... 378/38 |
| 2008/0063139 | A1 * | 3/2008 | Pantsar et al. ............ 378/40 |
| 2009/0168966 | A1 * | 7/2009 | Suzuki et al. ........... 378/116 |
| 2009/0274267 | A1 * | 11/2009 | Mandelkern et al. ...... 378/39 |
| 2009/0310741 | A1 * | 12/2009 | Borghese et al. ......... 378/37 |

OTHER PUBLICATIONS

Chamberlain WE. Fluoroscopes and fluoroscopy. Radiology 1942;38:383-413.

Mouyen F, Benz C, Sonnabend E, Lodter JP. Presentation and physical evaluation of RadioVisioGraphy. Oral Surg Oral Med Oral Pathol. Aug. 1989;68(2):238-42.

Ames JR, Johnson RP, Stevens EA. Computerized tomography in oral and maxillofacial surgery. J Oral Surg. Feb. 1980;38(2):145-9.

Mozzo P, et al. A new volumetric CT machine for dental imaging based on the cone-beam technique: preliminary results. Eur Radiol. 1998;8(9):1558-64.

Uzbelger-Feldman D, Susin C, Yang J. The use of fluoroscopy in dentistry: a systematic review. OOOOE, May 2008;vol. 105, Issue 4, p. e61.

Uzbelger D. Comparison between Medical Fluoroscopy, Digital Dental Imaging and Intraoral Radiography. IADR. J Dent Res 2005;84;701.

21 C.F.R. Part 1020. Federal Register. Electronic Products; Performance Standard for Diagnostic X-ray Systems and Their Major Components; Final Rule. 2005;70:33998-34042.

Antonuk LE, et al. Demonstration of megavoltage and diagnostic x-ray imaging with hydrogenated amorphous silicon arrays. Med Phys. Nov.-Dec. 1992;19(6):1455-66.

Zhao W, Rowlands JA. X-ray imaging using amorphous selenium: feasibility of a flat panel self-scanned detector for digital radiology. Med Phys. Oct. 1995;22(10):1595-604.

Nakagawa K, Aoki Y, Sasaki Y, Akanuma A, Mizuno S. C-MOS flat-panel sensor for real time X-ray imaging. Nippon Igaku Hoshasen Gakkai Zasshi. Feb. 1998;58(3):81-5.

Sakurai T, et al. The development of a new direct digital extra-oral radiographic system prototype using a thin-film transistor panel. Dentomaxillofac Radiol.1998;27(3):172-7.

Matsuura N, Zhao W, Huang Z, Rowlands JA. Digital radiology using active matrix readout: amplified pixel detector array for fluoroscopy. Med Phys. May 1999;26(5):672-81.

Leblans P, Struye L, Willems P. A new needle-crystalline computed radiography detector. J Digit Imaging. May 2000;13(2 Suppl 1):117-20.

Bury RF, et al. Initial technical and clinical evaluation of a new universal image receptor system. Eur Radiol. 2000;10(12):1983-7.

Baba R, Konno Y, Ueda K, Ikeda S. Comparison of flat-panel detector and image-intensifier detector for cone-beam CT. Comput Med Imaging Graph. May-Jun. 2000;26(3):153-8.

Srinivas Y, Wilson DL. Image quality evaluation of flat panel and image intensifier digital magnification in x-ray fluoroscopy. Med Phys. Jul. 2002;29(7):1611-21.

Hunt DC, Kirby SS, Rowlands JA. X-ray imaging with amorphous selenium: X-ray to charge conversion gain and avalanche multiplication gain. Med Phys. Nov. 2002;29(11):2464-71.

Hunt DC, et al. Evaluation of the imaging properties of an amorphous selenium-based flat panel detector for digital fluoroscopy. Med Phys. May 2004;31(5):1166-75.

El-Mohri Y, et al. Determination of the detective quantum efficiency of a prototype, megavoltage indirect detection, active matrix flat-panel imager. Med Phys. 2006 33(1):251.

* cited by examiner

DENTAL FLUOROSCOPIC IMAGING SYSTEM

This Non-Provisional U.S. patent application is based on the principles of the Provisional U.S. Patent Applications No. 61/201,744, 61/201,745, 61/201,746, 61/201,747 and 61/201,748 filled on Dec. 16, 2008.

1. CROSS REFERENCES

| | | |
|---|---|---|
| 4,593,400 | June 1986 | Mouyen |
| 4,965,455 | October 1990 | Schneider |
| 5,049,987 | September 1991 | Hoppenstein |
| 5,262,649 | November 1993 | Antonuk et al. |
| 5,382,798 | January 1995 | Mouyen |
| 5,434,418 | July 1995 | Schick |
| 5,510,623 | April 1996 | Sayed et al. |
| 5,519,751 | May 1996 | Yamamoto et al. |
| 5,610,404 | March 1997 | Possin |
| 5,648,654 | July 1997 | Possin |
| 5,693,948 | December 1997 | Sayed et al. |
| 5,773,832 | June 1998 | Sayed et al. |
| 5,834,782 | November 1998 | Schick et al. |
| 5,841,830 | November 1998 | Barni et al. |
| 5,912,942 | June 1999 | Schick et al. |
| 5,949,848 | September 1999 | Giblom |
| 5,962,856 | October 1999 | Zhao et al. |
| 6,404,854 | June 2002 | Carrol et al. |
| 6,543,936 | April 2003 | Feldman |
| 6,566,809 | May 2003 | Fuchs et al. |
| 6,717,174 | April 2004 | Karellas |
| 7,016,461 | March 2006 | Rotondo et al. |
| 7,136,452 | November 2006 | Spartiotis et al. |
| 7,197,109 | March 2007 | Rotondo et al. |
| 7,211,817 | May 2007 | Moody |
| 7,231,014 | June 2007 | Levi |
| 7,319,736 | January 2008 | Rotondo et al. |
| 7,322,746 | January 2008 | Beckhaus et al. |
| 7,323,692 | January 2008 | Rowlands et al. |
| 7,336,763 | February 2008 | Spartiotis et al. |
| 7,426,258 | September 2008 | Zweig |
| 7,563,026 | July 2009 | Mandelkern et al. |
| 7,596,205 | September 2009 | Zhang et al. |
| 7,608,834 | October 2009 | Boucly et. al |
| 7,615,754 | November 2009 | Liu et al. |
| 7,629,587 | December 2009 | Yagi |

2. CROSS REFERENCES INTERNATIONAL APPLICATIONS

| | | |
|---|---|---|
| WO/2004/110277 | December 2004 | Kim |
| WO/2005/072615 | August 2005 | Kim |
| WO/2005/110234 | November 2005 | Kim |

Other References

1.—Eisenberg R L. Radiology. An illustrated history. 1895 Centennial 1995: Mosby Year Book 1992; 4:51-78.

2.—Chamberlain W E. Fluoroscopes and fluoroscopy. Radiology 1942; 38:383-413.

3.—Mouyen F, Benz C, Sonnabend E, Lodter J P. Presentation and physical evaluation of RadioVisioGraphy. Oral Surg Oral Med Oral Pathol. 1989 August; 68(2):238-42.

4.—Ames J R, Johnson R P, Stevens E A. Computerized tomography in oral and maxillofacial surgery. J Oral Surg. 1980 February; 38(2):145-9.

5.—Mozzo P, Procacci C, Tacconi A, Martini P T, Andreis I A. A new volumetric CT machine for dental imaging based on the cone-beam technique: preliminary results. Eur Radiol. 1998; 8(9):1558-64.

6.—Uzbelger-Feldman D, Susin C, Yang J. The use of fluoroscopy in dentistry: a systematic review. OOOOE, May 2008; Volume 105, Issue 4, page e61.

7.—Uzbelger D. Comparison between Medical Fluoroscopy, Digital Dental Imaging and Intraoral Radiography. IADR. J Dent Res 2005; 84; 701. Available from: http://iadr.confex.com/iadr/2005Balt/techprogram/abstract_57264.htm 8.—C.F.R. Part 1020. Federal Register. June 2005; 70(111): 33998-34042.

9.—Antonuk L E, Boudry J, Huang W, McShan D L, Morton E J, Yorkston J, Longo M J, Street R A. Demonstration of megavoltage and diagnostic x-ray imaging with hydrogenated amorphous silicon arrays. Med Phys. 1992 November-December; 19(6):1455-66.

10.—Zhao W, Rowlands J A. X-ray imaging using amorphous selenium: feasibility of a flat panel self-scanned detector for digital radiology. Med Phys. 1995 October; 22(10):1595-604.

11.—Nakagawa K, Aoki Y, Sasaki Y, Akanuma A, Mizuno S. C-MOS flat-panel sensor for real time X-ray imaging. Nippon Igaku Hoshasen Gakkai Zasshi. 1998 February; 58(3): 81-5.

12.—Sakurai T, Matsuki T, Nakamura K, Kashima I, Lee D L, Cheung L K, Jeromin L S. The development of a new direct digital extra-oral radiographic system prototype using a thin-film transistor panel. Dentomaxillofac Radiol. 1998 May; 27(3):172-7.

13.—Matsuura N, Zhao W, Huang Z, Rowlands J A. Digital radiology using active matrix readout: amplified pixel detector array for fluoroscopy. Med Phys. 1999 May; 26(5):672-81.

14.—Leblans P, Struye L, Willems P. A new needle-crystalline computed radiography detector. J Digit Imaging. 2000 May; 13(2 Suppl 1):117-20.

15.—Bury R F, Cowen A R, Davies A G, Hawkridge P, Bruijns A J, von Reth E. Initial technical and clinical evaluation of a new universal image receptor system. Eur Radiol. 2000; 10(12):1983-7.

16.—Baba R, Konno Y, Ueda K, Ikeda S. Comparison of flat-panel detector and image-intensifier detector for cone-beam CT. Comput Med Imaging Graph. 2002 May-June; 26(3):153-8.

17.—Srinivas Y, Wilson D L. Image quality evaluation of flat panel and image intensifier digital magnification in x-ray fluoroscopy. Med Phys. 2002 July; 29(7):1611-21.

18.—Hunt D C, Kirby S S, Rowlands J A. X-ray imaging with amorphous selenium: X-ray to charge conversion gain and avalanche multiplication gain. Med Phys. 2002 November; 29(11):2464-71.

19.—Hunt D C, Tousignant O, Rowlands J A. Evaluation of the imaging properties of an amorphous selenium-based flat panel detector for digital fluoroscopy. Med Phys. 2004 May; 31(5): 1166-75.

20.—El-Mohri Y, Jee K W, Antonuk L E, Maolinbay M, Zhao Q. Determination of the detective quantum efficiency of a prototype, megavoltage indirect detection, active matrix flat-panel imager. Med Phys. 2006 January; 33(1):251.

3. BACKGROUND OF THE INVENTION

Before the discovery of electromagnetic radiation known as x-rays, techniques and procedures in the field of dentistry were based on purely empirical knowledge. On Nov. 8, 1895, William Conrad Roentgen announced the discovery of this new kind of radiation. Within fourteen days, Otto Walkhoff, a German dentist, took the first dental radiograph of his own mouth. Dr. William James had completed several dental radiographs five months later. In 1913, Coolidge improved the manufacturing techniques of the x-ray tube, which allowed for better control of the quality and quantity of radiographs. The panoramic x-ray device was invented in 1950. During many decades, the use of film-based radiography dominated these trends in dentistry.

Dental digital radiography is a form of x-ray imaging, where digital X-ray sensors are used instead of traditional photographic film. Advantages include time efficiency through bypassing chemical processing and the ability to digitally transfer and enhance images. Also less radiation can be used to produce a 2D still image of similar contrast to conventional film-based radiography. Some types of digital dental radiography sensors are small and thin enough that they can be placed intraorally or inside the mouth. Others are larger in size and are used extraorally or outside the mouth in order to obtain a dental image. The first intraoral X-rays imaging sensor available on the market was introduced following the principles described in U.S. Pat. No. 4,593,400 and U.S. Pat. No. 5,382,798 of Mouyen, 1986 and 1995 respectively based on a scintillating material and a charged coupled device (CCD) technology. Other inventions in the field used similar CCD sensors such as in U.S. Pat. No. 5,434,418 of Schick, 1995, U.S. Pat. No. 5,510,623 of Savag et al. and U.S. Pat. No. 5,693,948 of Sayed et al., 1996 and 1997 respectively and U.S. Pat. No. 5,519,751 of Yamamoto et al., 1996. Another particular type of digital system which uses a memory phosphor plate in place of the film is introduced in U.S. Pat. No. 4,965,455 of Schneider et al., 1990. The digitized images are stored, scanned and then displayed on the computer screen. This method is halfway between old film-based technology and current direct digital imaging technology. It is similar to the film process because it involves the same image support handling but differs because the chemical development process is replaced by the scanning process. The complementary metal-oxide-semiconductor (CMOS) active pixel sensor technology was proposed to dentistry in U.S. Pat. No. 5,912,942 of Schick et al., 1999 which provided advantages such as competitive wafer processing pricing, and on chip timing, control and processing electronics when compared to the CCD technology. Other inventions in the field utilizing similar CMOS technology are included in U.S. Pat. No. 6,404,854 of Carrol et al., 2002, U.S. Pat. No. 7,211,817 of Moody, 2007, U.S. Pat. No. 7,615,754 of Liu et al., 2009, and in U.S. Pat. No. 7,608,834 Boucly et al., 2009 which introduced some improvements through the description of the biCMOS technology combining bipolar transistors and CMOS devices. Due to the rigidity of these intraoral sensors which translated in patient's discomfort while placed inside the mouth, a flexible sensor using thin film transistors technology was devised in U.S. Pat. No. 7,563,026 of Mandelkern et al., 2009 trying to reproduce the comfort of conventional film.

On the other hand, the use of flat panel detectors in dentistry has been focused in the cephalometric, orthopantomographic, scannographic, linear tomographic, tomosynthetic and tomographic fields for 2D and 3D extraoral radiography. These principles are illustrated in the U.S. Pat. No. 5,834,782 of Schick et al., 1998, U.S. Pat. No. 7,016,461, U.S. Pat. No. 7,197,109 and U.S. Pat. No. 7,319,736 of Rotondo et al, 2006, 2007 and 2008 respectively, U.S. Pat. No. 7,136,452 and U.S. Pat. No. 7,336,763 of Spartiotis et al., 2006 and 2008 respectively and U.S. Pat. No. 7,322,746 of Beckhaus et al., 2008.

The problem with all these existing dental digital intraoral and extraoral radiography technologies is that their final outcome is either 2D or a 3D still image.

Fluoroscopy is a dynamic x-ray, or x-ray movie showing images of video frame rates. It differs from dental digital radiography in that dental digital radiography is static x-ray, or an x-ray picture. An analogy is that of a movie compared to a snapshot. The beginning of fluoroscopy can be traced back to 8 Nov. 1895 when Wilhelm Roentgen noticed a barium platinocyanide screen fluorescing as a result of being exposed to what he would later call x-rays. The fluoroscopic image obtained in this way was rather faint. Thomas Edison quickly discovered that calcium tungstate screens produced brighter images and is credited with designing and producing the first commercially available fluoroscope. The first fluoroscope for dental use was described by William Herbert Rollins in 1896. Due to the limited light produced from the fluorescent screens, early radiologists were required to sit in a darkened room in which the procedure was to be performed, getting their eyes accustomed to the dark and thereby increasing their sensitivity to the light. The placement of the radiologist behind the screen resulted in significant radiation doses to the radiologist. Red adaptation goggles were developed by Wilhelm Trendelenburg in 1916 to address the problem of dark adaptation of the eyes, The resulting red light from the goggles' filtration correctly sensitized the physician's eyes prior to the procedure while still allowing him to receive enough light to function normally. The invention of X-ray image intensifiers in the 1950s allowed the image on the screen to be visible under normal lighting conditions, as well as providing the option of recording the images with a conventional camera. Subsequent improvements included the coupling of, at first, video cameras and, later, video CCD cameras to permit recording of moving images and electronic storage of still images. Medical fluoroscopes also known as C-arms or mini C-arms are too large to fit in a dental operatory. The main reason is the size of one of their main components: >6 inches diameter image intensifiers. However, recent breakthroughs in imaging and night vision technologies made possible the miniaturization of the medical fluoroscope for dental use as disclosed in the U.S. Pat. No. 6,543,936 of Feldman, 2003 by using small image intensifiers. Night vision image intensifiers (18-40 mm diameter)—like those used for military purposes—can convert fluoroscopy's low-radiation beam—after going through the patient's dental area—on a vivid video image. This image can be captured by a video digital camera chip and then displayed in real-time video on a monitor. Consequently, this breakthrough has allowed the fluoroscopy technology to fit in a dental operatory. Another attempt to reduce the medical fluoroscope size is seen in foreign Patents No. WO/2004/110277, WO/2005/072615 and WO/2005/110234 of Kim, 2004, 2005 and 2005 respectively. Despite these efforts, the image receptor configuration using the image intensifier and camera is still too bulky to be used inside the mouth and not ergonomic for the dentist to be placed extraorally while performing treatments on patients. Also, the proposed configurations in previous inventions only disclose the use of fluoroscopy in a 2D approach using image intensifiers.

However, more modern medical technology improvements in flat panel detectors have allowed for increased sensitivity to X-rays, and therefore the potential to reduce patient radiation dose. The introduction of flat-panel detectors in for 2D fluoroscopy in medicine as illustrated in the U.S. Pat. No. 5,262, 649 of Antonuk et al., 1993, U.S. Pat. No. 5,610,404 and U.S. Pat. No. 5,648,654 of Possin, 1997 respectively, U.S. Pat. No. 5,773,832 of Sayed et al., 1998, U.S. Pat. No. 5,949,848 of Giblom, 1999, U.S. Pat. No. 5,962,856 of Zhao et al., 1999, U.S. Pat. No. 6,566,809 of Fuchs et al., 2003, U.S. Pat. No. 6,717,174 of Karellas, 2004, U.S. Pat. No. 7,231,014 of Levy, 2007, U.S. Pat. No. 7,323,692 of Rowlands et al., 2008, U.S. Pat. No. 7,426,258 of Zweig, 2008, U.S. Pat. No. 7,629,587 of Yagi, 2009 allows for the replacement of the image intensifier in the medical fluoroscope design. Temporal resolution is also improved over image intensifiers, reducing motion blurring. Contrast ratio is also improved over image intensifiers: flat-panel detectors are linear over very wide latitude, whereas image intensifiers have a maximum contrast ratio. Medical fluoroscopy 3D approaches have been described in the U.S. Pat. No. 5,049,987 of Hoppenstein, 1991 utilizing a plurality of image capture devices arranged in a predetermined pattern, in the U.S. Pat. No. 5,841,830 of Barni et al., 1998 where a motor is used to rotate the emitter and detector around the patient body and in the U.S. Pat. No. 7,596,205 of Zhang et al., 2009 in which the X-ray radiography unit irradiates a subject with X-rays from first X-ray tube to obtain an X-ray radiographic image. The X-ray CT unit irradiates the subject with X-rays from the second X-ray tube and acquires projection data from a beam of the X-rays that has passed through the subject, to reconstruct an image using the acquired projection data, and to obtain a tomographic image.

As has been shown, all these inventions are designed to be used on a medical setting. They are too large to be used for dental purposes. Consequently, none of these dental and medical technologies offer a flat panel, an emitter in a C-arm/U-arm and an O-arm configuration suitable for 2D and 3D dental fluoroscopy.

4. BRIEF SUMMARY OF THE INVENTION

The present invention relates generally to the field of diagnostic radiology, and specifically to a dental fluoroscopic imaging system apparatus using flat panel detectors and emitters in C-arm/U-arm, O-arm configurations suitable for two dimensional (2D) and three dimensional (3D) dental fluoroscopy and the method of producing the same.

6. DETAILED DESCRIPTION OF THE INVENTION

Figure 1:
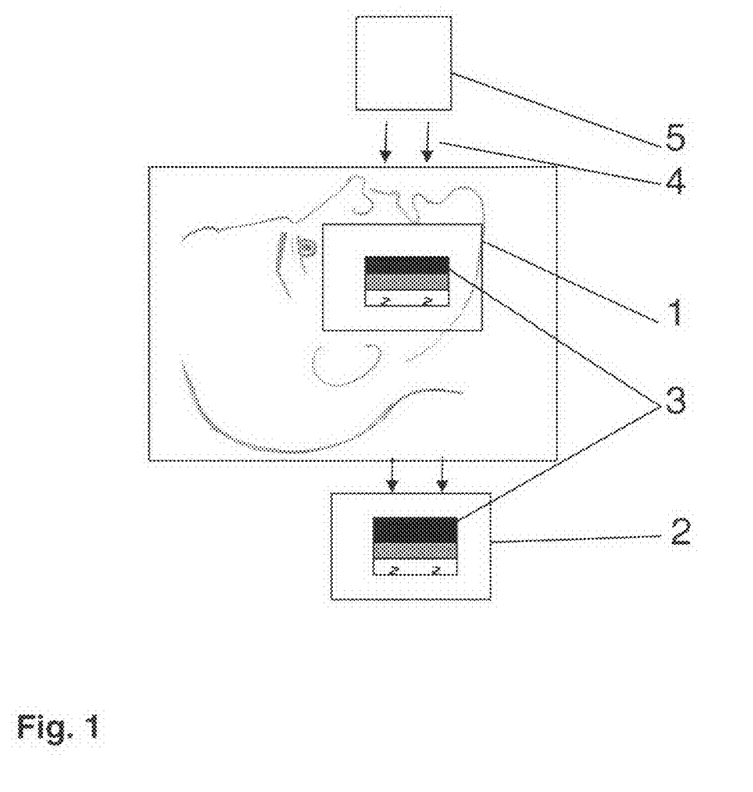
FIG. 1 is a side schematic view of the configuration of the intraoral and extraoral flat panel detectors following the principles of the herein invention.
Figure 2:
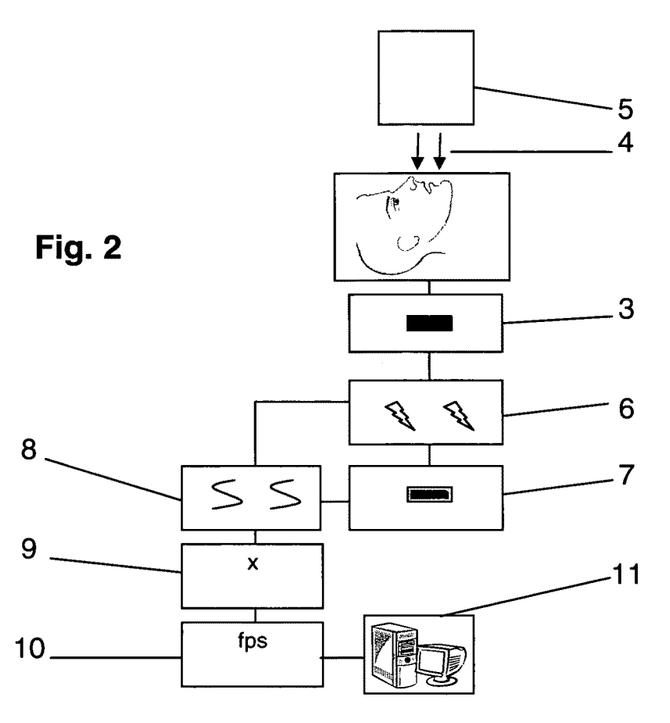
FIG. 2 is a side schematic view of the configuration of the dental fluoroscopic imaging system according to the principles of the invention.

As described in FIGS. 1 and 2, this invention discloses a dental fluoroscopic imaging system comprised by an intraoral 1 and extraoral 2 flat panel detectors utilizing an x-ray converter 3 which includes a semiconductor of amorphous selenium (a-se), or a material such as NaI, NaI(TI), higher-Z bismuth germinate (BGO), $BaF_2$, $CaF_2(Eu)$, high-purity germanium HPGe, Cesium Iodide (CsI), CsI(TI), CsI(Na), $LaCl_3(Ce)$, $LaBr_3(Ce)$, $LuI_3$, $Lu_2SiO_5$, Gadolinium Oxysulphide (GSO), $Lu_{1.8}Y_{0.2}SiO_5(Ce)$, amorphous silicon (a-si), poly-si, metal ceramic, $CdWO_4$, $CaWO_4$, linear photodiode array (PDA), Si(Li), CdTe, CdZnTe, CZT, CdSe, CdS, Se, $PbI_2$, PbTe, HgTe, $HgI_2$, ZnS, ZnTe, $ZnWO_4$, GaP, AlSb, YAG(Ce), $Gd_2O_2S$, in order to transform the low dose gamma rays or x-rays beam 4 received from a high frequency direct current (DC) emitter 5 after going through the dental examination area into electrical signals or a light image 6 consequent with the radiographed image. The emitter 5 may contain a radioactive source, a radiation generator, a gamma rays source, a charged particles radiation, a neutral particles radiation, a Marx generator, a device based on bremsstrahlung radiation, a tape on a vacuum system, an X-ray tube or a Cold Cathode X-ray tube. The emitter focal spot size is within the range from 0.005 to 0.8 mm with a target angle range from 0 to 30 degrees. The voltage peaks will be selected within the range from 35 to 95 kVp and while the current peaks will be between 0.0001 to 10 mA. The emitter 5 will allow an x-ray beam with a continuous rate from 1 to 50 ms or with a pulse width range from 1 to 100 pulses/sec.

Figure 3:
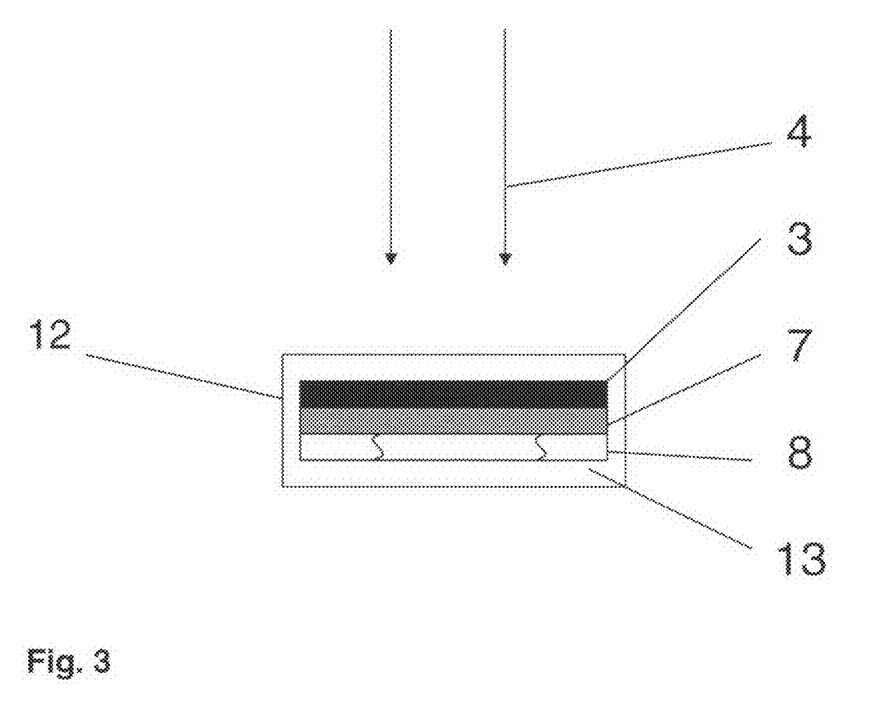
FIG. 3 is a side schematic view of the device of FIG. 1, showing the configuration of the intraoral and extraoral flat panel detectors.

The x-ray converter 3 material may be coupled to a plate 7 such as a dielectric and top electrode layers material, fiber optic, aluminum, metal ceramic, glass and amorphous carbon or by a photodiode array of amorphous selenium or amorphous silicon. The electrical signals or light image 6 are transmitted to a collector 8 made of an active matrix array or an amplified pixel detector array (APDA) of amorphous selenium or amorphous silicon thin film transistor and storage capacitor (TFT), or Electrometer Probes, a Charged Coupled Device type (CCD), an Electron Multiplied chip, a Thinned Back Illuminated chip, an active pixel sensor Complementary Metal Oxide Semiconductor (CMOS) array or a biCMOS based on silicon-germanium-carbon (SiGe:C) technology. When the collector 8 is activated by an address electrical signals or light image 6 from the high speed processing unit 9 the electrical signals that are read out in response to this address signals are amplified and sent to a transmitter 10 such as an analog to digital converter unit. The transmitter 10 is designed to convert to digital and transfer digital images sequentially to a host 11 computer and software which enables to acquire, process, transform, record, freeze and enhance 2D and 3D images of video frame rates ranging from 3 to 100 frames per second (fps). The improved method of this invention allows obtaining dental fluoroscopy images with a better spatial resolution, high quantum efficiency, high gain, and low noise, a high image signal-to-noise ratios, high dynamic range and high speed on the same detector. The method described provides an intraoral 1 and extraoral 2 flat panel detectors without the needs of being coupled to an image intensifier unit, lenses and fiber optic taper. In consequence, the size and the costs of the system are considerably reduced. Following these principles, dental procedures can be observed at the same time that they are being performed or in real time 2D or 3D dental fluoroscopy. The intraoral 1 and extraoral 2 flat panel detectors are included in a biocompatible housing 12 that fulfills the EN30993-1 Biological Testing of Dental and Medical Devices and with the ISO standards that have a feature of not allowing the pass of the light by its fore face, but allowing the pass of the gamma rays or x-rays beam 4. The back face of the detector herein can be covered in its internal wall by a thin sheet 13 made of lead, x-rays attenuating plastic or other material which can function as a shield to stop the gamma rays or x-rays beam 4 and to minimize scattered radiation as shown in FIG. 3.

The intraoral flat panel detector 1 can be presented in three different types which correspond with the conventional film sizes available in dentistry. Type 1: Periapical, Type 2: Bite Wing and Type 3: Occlusal in sizes 0, 1, 2, 3 and 4 ranging from 22×35 millimeters to 57×76 millimeters of overall dimension. The thickness of the intraoral flat panel detector 1 can be adequate to be placed inside the patient's mouth and be maintained by any x-ray intraoral sensor positioning system.

Figure 4:
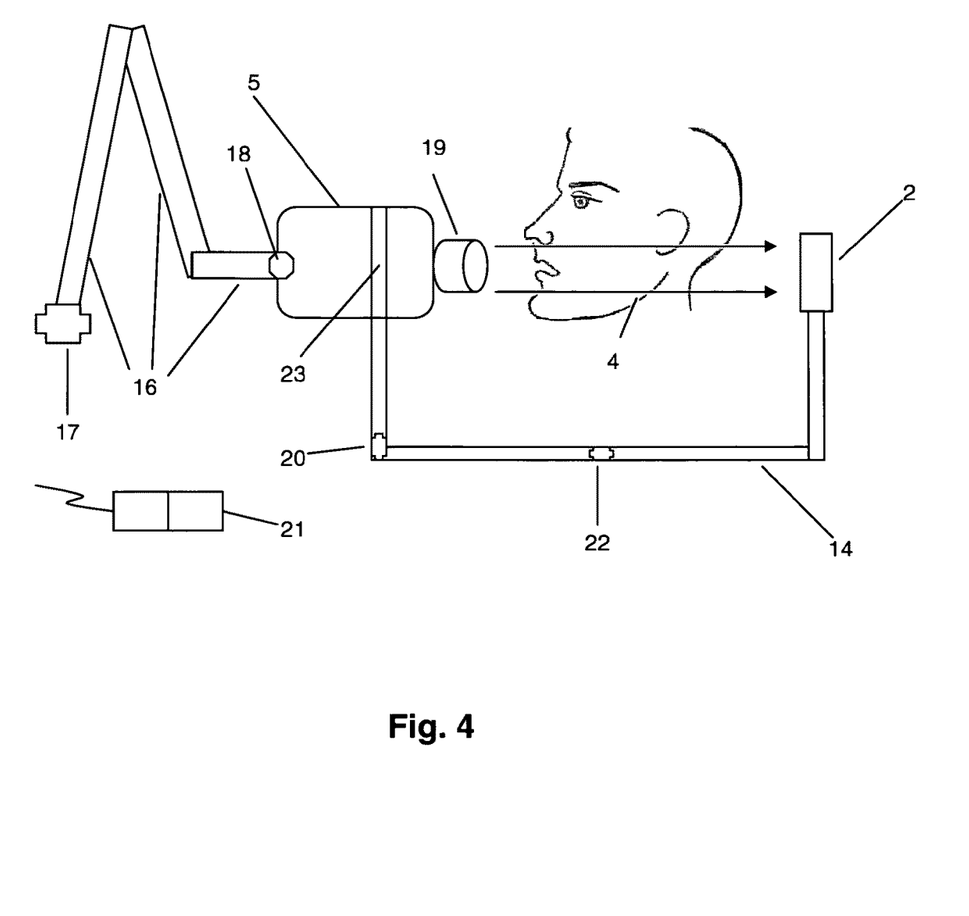
FIG. 4 is a side outer view of the dental fluoroscopic imaging system showing most of the components of the C-arm/U-arm assembly and method of using the same.
Figure 5:
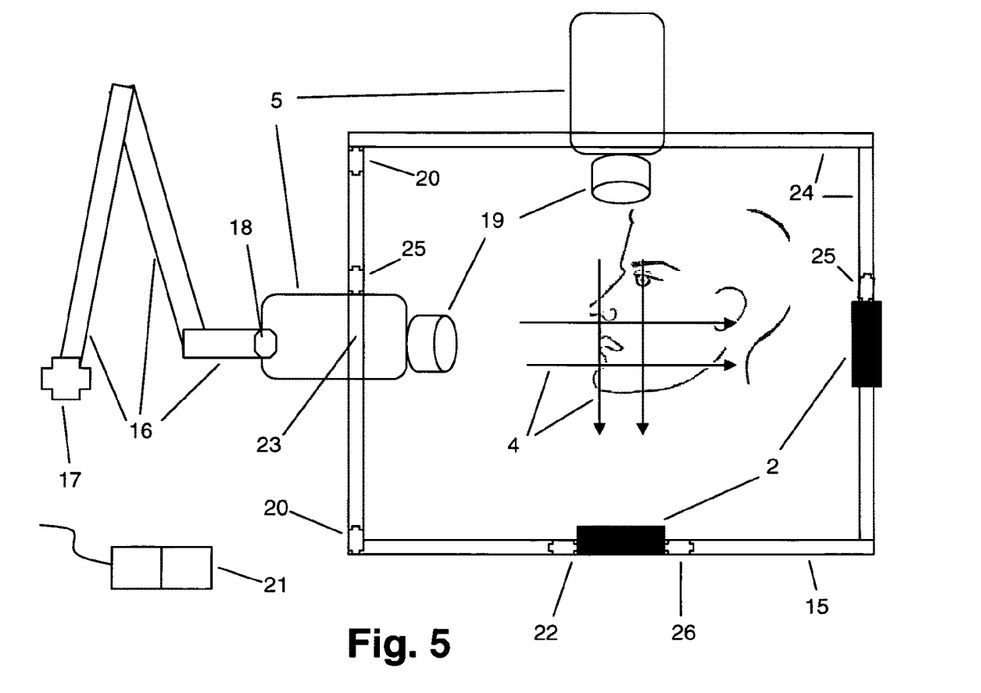
FIG. 5 is a side outer view of the dental fluoroscopic imaging system showing most of the components of the O-arm assembly and method of using the same.

The extraoral flat panel detector 2 can have an active area ranging from 40×40 to 60×60 millimeters and can be attached along with the emitter 5 to a C-Arm/U-Arm 14 or O-Arm 15 assemblies. Tin FIGS. 4 and 5 it is shown how this emitter 5, with all its components and parts, is attached to the mechanic arms 16, which are capable to extend, fold, and go up and down and to mobilize to the left and to the right. These mechanic arms 16 can be fixed through an attachment 17 on the dental office's wall, roof and/or any dental unit. In addition if it is desirable the attachment 17 could be used to couple the system with a mobile unit to make the apparatus portable. Between the mechanical arms 16 and the posterior side of the emitter 5 there is a spin attachment 18, which allows the movement up, down, left and right of the emitter 5. Thereafter, the intraoral flat panel detector 1 is placed inside the patient's mouth in the selected place with a film positioning device in order to place the collimator cone 19 aiming to the direction to the area to be radiographed with the desired angulation. For this purposes, the C-arm/U-arm and the O-arm are provided with a hinge 20 which allows folding back the extraoral flat panel detector. The activation of for the dental fluoroscopic imaging system is based on a wireless or cable-based pedal control 21. In FIGS. 4 and 5 it is shown the C-Arm/U-Arm 14 and O-arm 15 interlocks 22 which allows to fix the distance between the emitter 5 and the extraoral flat panel detector 2. Thereby, the C-Arm/U-Arm and the O-arm 15 assemblies can be adjusted to take into consideration the patient's size and the X-ray beam 4 angle. In addition, the emitter is attached to the mechanic arms 16 by means of a rotational axis 23 which allows the C-arm/U-arm 14 and O-arm 15 to rotate up to 360 degrees around the emitter. The C-arm/U-arm 14 can be upgraded to an O-arm/U-arm 15 configuration by connecting the C-arm/U-arm 24 portion which is not attached to the mechanic arms 16 through the attaches 25 and an extraoral flat panel detector 2 through the flat panel attachment 26.

If a single emitter 5 and a single extraoral flat panel detector 2 are positioned parallel facing one to each other and attached to a C-arm/U-arm 14 configuration a 2D fluoroscopic image will be obtained as shown in FIG. 4. In order to obtain a 3D dental fluoroscopic image, two emitters 5 and two extraoral flat panel detectors 2 may be used in the same way as described for the C-arm/U-arm configuration but attached to an O-arm 15 in a cross approach and emitting x-rays beams 4 which intercepts in a perpendicular point which corresponds to the patient examination area as illustrated in FIG. 5. As a result, two x-rays beams 4 from two different emitters 5 after going through the dental examination area in a perpendicular point are received by two different extraoral flat panel detectors 2. There, the x-rays images consequent with the patient radiographed area are converted into a light or electrical signals, collected, amplified and processed as described herein. Then, they are transmitted at the same time to a host 11 computer and software which enables processing two 2D images of video frame rates received from two different planes on 3D images of video frame rates.

These improved dental fluoroscopic imaging system enhanced productivity capabilities are because they fulfill the Digital Imaging and Communication in Medicine (DICOM) and Picture Archiving and Communication System (PACS) digital image format standards for x-rays image capture. With these digital image capture systems the image data sent to workstations, printers and files is always identical to the original.

In order to reduce the level of the exposure to radiation of the patient and the operator, it is normally required to use mechanical barriers of radiological protection and to fulfill the requirements of the Federal Food and Drug Administration Regulations (FDA), that include the warnings as hearing alarms that indicate when the exposure levels of the skin exceed the 5 R/min for fluoroscopy. According to the Dose Rate Guidance Levels for Fluoroscopy for a Typical Adult Patient of the IAEA, 2004, the doses allowed in the normal fluoroscopic operation mode are up to 25 mGy per min.

It is to be understood that the above-described arrangements are only illustrative of the application of the principles of the present invention. Numerous modifications and alternative arrangements may be devised by those skilled in the art without departing from the spirit and scope of the present invention.

The invention claimed is:

1. A fluoroscopic imaging method performed during a dental procedure for providing real-time video display of the dental procedure, comprising the steps of:
   (a) causing a beam of electromagnetic radiation to travel,
      (1) from an emitter,
      (2) through an area in which the dental procedure is being performed on a patient,
      (3) to a flat panel detector;
   (b) within the flat panel detector, performing the steps of,
      (1) generating digital data representative of digital images based on the electromagnetic radiation of the beam that is received by the flat panel detector, and
      (2) transmitting the digital data representative of digital images from the flat panel detector; and
   (c) at a computer, performing the steps of,
      (1) receiving the digital data representative of digital images transmitted from the flat panel detector, and
      (2) processing the digital data representative of digital images transmitted from the flat panel detector for display of digital images in the form of real-time video of the dental procedure;
   (d) using the processed data of said step (c)(2), displaying the real-time video of the dental procedure to a person at the location of the digital procedure;
   (e) wherein during said steps (a) through (d) the emitter and the flat panel detector do not concurrently rotate about the area in which the dental procedure is being performed;
   (f) wherein said steps (a) through (d) are performed such that the real-time video has a video frame rate of between 1 and 100 images per second; and
   (g) wherein the emitter is operated at voltage peaks within the range from 35 to 95 kVp and at current peaks between 0.0001 to 10 mA, and provides a beam with a continuous rate from 1 to 50 ms or with a pulse width range from 1 to 100 pulses/second, whereby low dose electromagnetic radiation is emitted during performance of said step (a).

2. The fluoroscopic imaging method of claim 1, wherein said step (d) comprises displaying the real-time video of the dental procedure to the person performing the procedure.

3. The fluoroscopic imaging method of claim 1, when the flat panel detector is an intraoral detector.

4. The fluoroscopic imaging method of claim 1, when the flat panel detector is an extraoral detector.

5. The fluoroscopic imaging method of claim 1, wherein the step performed at the computer of processing the data representative of digital images comprises transforming the digital data representative of digital images transmitted from the flat panel detector.

6. The fluoroscopic imaging method of claim 1, wherein the step performed at the computer of processing the data representative of digital images comprises recording the digital data representative of digital images transmitted from the flat panel detector.

7. The fluoroscopic imaging method of claim 1, wherein the step performed at the computer of processing the data representative of digital images comprises processing the digital data representative of digital images transmitted from the flat panel detector so as to enhance the represented digital images.

8. The fluoroscopic imaging method of claim 1, wherein the step performed at the computer of processing the data representative of digital images comprises compiling a series of the represented digital images into a video having a video frame rate ranging from 1 to 100 frames per second.

9. A fluoroscopic imaging method, comprising the steps of:
 (a) causing a beam of electromagnetic radiation to travel,
  (1) from a emitter,
  (2) through an area in which the dental procedure is being performed on a patient,
  (3) to a flat panel detector;
 (b) within the flat panel detector, performing the steps of,
  (1) transforming electromagnetic radiation of the beam that is received into electrical signals,
  (2) amplifying the electrical signals,
  (3) converting the amplified electrical signals into digital data representative of a digital image, and
  (4) transmitting the digital data representative of the digital image from the flat panel detector;
 (c) at a computer, performing the steps of,
  (1) receiving the digital data representative of the digital image transmitted from the flat panel detector, and
  (2) generating an image based at least in part on the received data representative of the digital image for display of digital images in the form of real-time video of the dental procedure; and
 (d) repeating said steps (a) through (c) and, using the generated images of said step (c)(2), displaying real-time video of the dental procedure to a person at the location of the digital procedure;
 (e) wherein during performance of said steps (a)-(d) the emitter and the flat panel detector do not concurrently rotate about the area in which the dental procedure is being performed; and
 (f) wherein during performance of said steps (a)-(d) the emitter is operated at voltage peaks within the range from 35 to 95 kVp and at current peaks between 0.0001 to 10 mA, and provides an beam with a continuous rate from 1 to 50 ms or with a pulse width range from 1 to 100 pulses/second, whereby low dose electromagnetic radiation is emitted during performance of said step (a).

10. The fluoroscopic imaging method of claim 9, further comprising, while performing said steps (a) through (c), repeatedly performing the steps of,
 (g) causing a second beam of electromagnetic radiation to travel,
  (1) from a second emitter,
  (2) through the area in which the dental procedure is being performed on the patient,
  (3) to a second flat panel detector;
 (h) within the second flat panel detector, performing the steps of,
  (1) transforming electromagnetic radiation of the second beam that is received into electrical signals,
  (2) amplifying the electrical signals,
  (3) converting the amplified electrical signals into digital data representative of a second digital image, and
  (4) transmitting the digital data representative of the second digital image from the second flat panel detector; and
 (i) at the computer, performing the steps of,
  (1) receiving the digital data representative of the second digital image transmitted from the second flat panel detector, and
  (2) generating an image based at least in part on the received data representative of the second digital image for the display of digital images in the form of the real-time video of the dental procedure;
 (j) wherein said step (d) further comprises using the generated images of said step (i)(2).

11. The fluoroscopic imaging method of claim 10, wherein said steps (a)-(i) are performed such that the real-time video has a video frame rate of between 1 and 100 images per second.

12. The fluoroscopic imaging method of claim 10, wherein said step (d) comprises displaying the real-time video of the dental procedure to the person performing the procedure.

13. The fluoroscopic imaging method of claim 10, wherein at least one of the two flat panel detectors is an intraoral detector.

14. The fluoroscopic imaging method of claim 10, wherein at least one of the two flat panel detectors is an extraoral detector.

15. The fluoroscopic imaging method of claim 10, wherein during performance of said steps the emitters and the flat panel detectors do not concurrently rotate about the area in which the dental procedure is being performed.

16. The fluoroscopic imaging method of claim 10, wherein during performance of said steps each of the emitters is operated at voltage peaks within the range from 35 to 95 kVp and at current peaks between 0.0001 to 10 mA, and provides an beam with a continuous rate from 1 to 50 ms or with a pulse width range from 1 to 100 pulses/second, whereby low dose electromagnetic radiation is emitted.

17. A fluoroscopic imaging method, comprising the steps of:
 (a) causing,
  (1) a first beam of electromagnetic radiation to travel,
   (A) from a first emitter,
   (B) through an area in which the dental procedure is being performed on a patient,
   (C) to a first flat panel detector;
  (2) a second beam of electromagnetic radiation to travel,
   (A) from a second emitter,
   (B) through the area in which the dental procedure is being performed on a patient,
   (C) to a second flat panel detector;
 (b) within the first flat panel detector, performing the steps of,
  (1) transforming electromagnetic radiation of the first beam that is received into electrical signals,
  (2) amplifying the electrical signals,
  (3) converting the amplified electrical signals into digital data representative of a first digital image, and
  (4) transmitting the digital data representative of the first digital image from the first flat panel detector;

(c) within the second flat panel detector, performing the steps of,
  (1) transforming electromagnetic radiation of the second beam that is received into electrical signals,
  (2) amplifying the electrical signals,
  (3) converting the amplified electrical signals into digital data representative of a second digital image, and
  (4) transmitting the digital data representative of the second digital image from the second flat panel detector;
(d) at a computer, performing the steps of,
  (1) receiving the digital data representative of the first digital image transmitted from the first flat panel detector and the digital data representative of the second digital image transmitted from the second flat panel detector, and
  (2) generating an image based at least in part on the received data representative of the first digital image and the received data representative of the second digital image for display of digital images in the form of real-time video of the dental procedure; and
(e) repeating said steps (a) through (d) and, using the generated images of said step (d)(2), displaying real-time video of the dental procedure to a person at the location of the digital procedure; and,
(f) wherein during performance of steps (a) through (d), the emitters and the flat panel detectors do not concurrently rotate about the area in which the dental procedure is being performed.

18. The fluoroscopic imaging method of claim 17, wherein the real-time video that is displayed is a 3D video.

19. The fluoroscopic imaging method of claim 17, wherein during performance of said steps each of the emitters is operated at voltage peaks within the range from 35 to 95 kVp and at current peaks between 0.0001 to 10 mA, and provides an beam with a continuous rate from 1 to 50 ms or with a pulse width range from 1 to 100 pulses/second, whereby low dose electromagnetic radiation is emitted.

20. A fluoroscopic imaging method, comprising the steps of:
(a) causing a first beam of electromagnetic radiation to travel from a first emitter through an examination area to a first flat panel detector;
(b) within the first flat panel detector, performing the steps of,
  (i) transforming electromagnetic radiation of the first beam that is received into electrical signals,
  (ii) amplifying the electrical signals,
  (iii) converting the amplified electrical signals into digital data representative of a first digital image, and
  (iv) transmitting the digital data representative of the first digital image from the first flat panel detector; and
(c) at a computer, performing the steps of,
  (i) receiving the digital data representative of the first digital image transmitted from the first flat panel detector, and
  (ii) generating an image based at least in part on the received data representative of the first digital image; and
further comprising the steps of,
(d) causing a second beam of electromagnetic radiation to travel from a second emitter through the examination area to a second flat panel detector;
(e) within the second flat panel detector, performing the steps of,
  (i) transforming electromagnetic radiation of the second beam that is received into electrical signals,
  (ii) amplifying the electrical signals,
  (iii) converting the amplified electrical signals into digital data representative of a second digital image, and
  (iv) transmitting the digital data representative of the second digital image from the second flat panel detector; and
(f) at the computer, performing the steps of,
  (i) receiving the digital data representative of the second digital image transmitted from the second flat panel detector, and
  (ii) generating the image based at least in part on the received data representative of the second digital image;
(g) wherein the first beam and the second beam intersect generally orthogonally at the examination area.

21. A fluoroscopic imaging method, comprising the steps of:
(a) causing a first beam of electromagnetic radiation to travel from a first emitter through an examination area to a first flat panel detector;
(b) within the first flat panel detector, performing the steps of,
  (i) transforming electromagnetic radiation of the first beam that is received into electrical signals,
  (ii) amplifying the electrical signals,
  (iii) converting the amplified electrical signals into digital data representative of a first digital image, and
  (iv) transmitting the digital data representative of the first digital image from the first flat panel detector; and
(c) at a computer, performing the steps of,
  (i) receiving the digital data representative of the first digital image transmitted from the first flat panel detector, and
  (ii) generating an image based at least in part on the received data representative of the first digital image; and
further comprising the steps of,
(d) causing a second beam of electromagnetic radiation to travel from a second emitter through the examination area to a second flat panel detector;
(e) within the second flat panel detector, performing the steps of,
  (i) transforming electromagnetic radiation of the second beam that is received into electrical signals,
  (ii) amplifying the electrical signals,
  (iii) converting the amplified electrical signals into digital data representative of a second digital image, and
  (iv) transmitting the digital data representative of the second digital image from the second flat panel detector; and
(f) at the computer, performing the steps of,
  (i) receiving the digital data representative of the second digital image transmitted from the second flat panel detector, and
  (ii) generating the image based at least in part on the received data representative of the second digital image;
(g) wherein the digital data representative of the first digital image is transmitted from the first flat panel detector at the same time that the digital data representative of the second digital image is transmitted from the second flat panel detector.

22. A fluoroscopic imaging method, comprising the steps of:
  (a) causing a first beam of electromagnetic radiation to travel from a first emitter through an examination area to a first flat panel detector;
  (b) within the first flat panel detector, performing the steps of,
    (i) transforming electromagnetic radiation of the first beam that is received into electrical signals,
    (ii) amplifying the electrical signals,
    (iii) converting the amplified electrical signals into digital data representative of a first digital image, and
    (iv) transmitting the digital data representative of the first digital image from the first flat panel detector; and
  (c) at a computer, performing the steps of,
    (i) receiving the digital data representative of the first digital image transmitted from the first flat panel detector, and
    (ii) generating an image based at least in part on the received data representative of the first digital image; and
  further comprising the steps of,
  (d) causing a second beam of electromagnetic radiation to travel from a second emitter through the examination area to a second flat panel detector;
  (e) within the second flat panel detector, performing the steps of,
    (i) transforming electromagnetic radiation of the second beam that is received into electrical signals,
    (ii) amplifying the electrical signals,
    (iii) converting the amplified electrical signals into digital data representative of a second digital image, and
    (iv) transmitting the digital data representative of the second digital image from the second flat panel detector; and
  (f) at the computer, performing the steps of,
    (i) receiving the digital data representative of the second digital image transmitted from the second flat panel detector, and
    (ii) generating the image based at least in part on the received data representative of the second digital image;
  (g) wherein the image is displayed to a user in real time.

23. A fluoroscopic imaging method, comprising the steps of:
  (a) causing a first beam of electromagnetic radiation to travel from a first emitter through an examination area to a first flat panel detector;
  (b) within the first flat panel detector, performing the steps of,
    (i) transforming electromagnetic radiation of the first beam that is received into electrical signals,
    (ii) amplifying the electrical signals,
    (iii) converting the amplified electrical signals into digital data representative of digital images, and
    (iv) transmitting the digital data representative of digital images from the first flat panel detector; and
  (c) at a computer, performing the steps of,
    (i) receiving the digital data representative of digital images transmitted from the first flat panel detector, and
    (ii) displaying a video to a user in real based at least in part on the digital data representative of digital images that is received from the first flat panel detector; and
  further comprising the steps of,
  (d) causing a second beam of electromagnetic radiation to travel from a second emitter through the examination area to a second flat panel detector;
  (e) within the second flat panel detector, performing the steps of,
    (i) transforming electromagnetic radiation of the second beam that is received into electrical signals,
    (ii) amplifying the electrical signals,
    (iii) converting the amplified electrical signals into digital data representative of a second digital image, and
    (iv) transmitting the digital data representative of the second digital image from the second flat panel detector; and
  (f) at the computer, performing the steps of,
    (i) receiving the digital data representative of digital images transmitted from the second flat panel detector, and
    (ii) displaying the video to the user in real based in part on the digital data representative of digital images that is received from the second flat panel detector.

* * * * *

UNITED STATES PATENT AND TRADEMARK OFFICE
CERTIFICATE OF CORRECTION

PATENT NO. : 8,430,563 B2
APPLICATION NO. : 12/653964
DATED : April 30, 2013
INVENTOR(S) : Daniel Uzbelger Feldman It is certified that error appears in the above-identified patent and that said Letters Patent is hereby corrected as shown below:

In the Claims:

Column 14, Claim 23, Subpart (c)(ii), Line 19    After "in real" insert -- time --

Column 14, Claim 23, Subpart (f)(ii), Line 40    After "in real" insert -- time --

Signed and Sealed this
Twenty-second Day of October, 2013

Teresa Stanek Rea
*Deputy Director of the United States Patent and Trademark Office*